United States Patent [19]

Roizman

[11] Patent Number: 5,288,641
[45] Date of Patent: Feb. 22, 1994

[54] HERPES SIMPLEX VIRUS AS A VECTOR

[75] Inventor: Bernard Roizman, Chicago, Ill.

[73] Assignee: Arch Development Corporation, Chicago, Ill.

[21] Appl. No.: 923,015

[22] Filed: Jul. 30, 1992

Related U.S. Application Data

[63] Continuation of Ser. No. 455,771, Dec. 28, 1989, abandoned, which is a continuation of Ser. No. 616,930, Jun. 4, 1984, abandoned.

[51] Int. Cl.$^5$ .............. C12N 15/86; C12N 15/09; C12P 21/00
[52] U.S. Cl. .............. 435/320.1; 435/69.1; 435/172.1; 435/172.3
[58] Field of Search .............. 435/69.1, 320.1, 172.3, 435/172.1

[56] References Cited

U.S. PATENT DOCUMENTS

| 4,603,112 | 7/1986 | Paoletti et al. | 424/89 |
| 4,769,331 | 9/1988 | Roizman et al. | 435/172.3 |

FOREIGN PATENT DOCUMENTS

| 74808 | 3/1983 | European Pat. Off. . |
| 83286 | 7/1983 | European Pat. Off. . |
| WO832393 | 7/1983 | PCT Int'l Appl. . |
| WO842077 | 6/1984 | PCT Int'l Appl. . |

OTHER PUBLICATIONS

Mackem et al. 1982, J. Virology 44:939.
Shih et al. 1984, PNAS 81:5867.
McKnight et al. 1982, Science 217:316.
Pourcel et al. 1982, J. Virology 42:100.
Tackney, et al., Journal of Virology, vol. 52, No. 2, pp. 606–614 (Nov. 1984).
Kwong, et al., Journal of Virology, vol. 62, No. 3, pp. 912-921 (Mar. 1988).
Wagner et al, Proc. Natl. Acad. Sci. USA, vol. 78, pp. 1441–1445 (1981).
McKnight, Nucleic Acids Res., vol. 8, pp. 5949-5964 (1980).
Mocarski et al, Cell, vol. 22, pp. 243-255 (1980).
Post et al, Proc. Natl. Acad. Sci. USA, vol. 77, No. 7, pp. 4201–4205 (1980).
Post et al, Cell, vol. 24, pp. 555-565 (1981).
Post et al, Cell, vol. 25, pp. 227-232 (1981).
Ruyechan et al, J. Virol., vol. 29, pp. 677–697 (1979).
Dane et al, Lancet, vol. 1, pp. 695-698 (1970).
Knipe et al, Proc. Natl. Acad. Sci. USA, vol. 75, pp. 3896–3900 (1978).
Poffenberger et al, Proc. Natl. Acad. Sci. USA, vol. 80, pp. 2690-2694 (May 1983).
Dubois et al, Proc. Natl. Acad. Sci. USA, vol. 77, No. 81 pp. 4549–4553 (1980).
Post et al, Molecular and Cellular Biology, vol. 2, No. 3, pp. 233-240 (1982).
Roizman et al, Develop. Biol. Standard., vol. 52, pp. 287-304 (1982).
Smith et al, Nature, vol. 302, pp. 490–495 (Apr. 1983).
Herz et al, Cell, vol. 33, pp. 145-151 (May 1983).
Paoletti et al, Proc. Natl. Acad. Sci. USA, vol. 81, pp. 193-197 (Jan. 1984).
Baines et al., Journal of Virology, vol. 65, No. 12, pp. 6414–6424, 1991.
Baines et al., Journal of Virology, vol. 65, No. 2, pp. 938–944, 1991.
Barker et al., Virology, vol. 177, pp. 684–691, 1990.
Chou et al., Journal of Virology, vol. 64, No. 3, pp. 1014–1020, 1990.

(List continued on next page.)

Primary Examiner—Richard A. Schwartz
Assistant Examiner—David Guzo
Attorney, Agent, or Firm—Marshall, O'Toole, Gerstein, Murray & Borun

[57] ABSTRACT

A foreign gene is inserted into a viral genome under the control of promoter-regulatory regions of the genome, thus providing a vector for the expression of the foreign gene. DNA constructs, plasmid vectors containing the constructs useful for expression of the foreign gene, recombinant viruses produced with the vector, and associated methods are disclosed.

62 Claims, 5 Drawing Sheets

OTHER PUBLICATIONS

Heine et al., *Journal of Virology*, vol. 14, No. 3, pp. 640–651, 1974.

Jenkins et al., *Proc. Natl. Acad. Sci. USA*, vol. 82, pp. 4773–4777, 1985.

Longnecker et al., *Proc. Natl. Acad. Sci. USA*, vol. 84, pp. 4303–4307, 1987.

Longnecker et al., *Science*, vol. 236, pp. 573–576, 1987.

Longnecker et al., *Journal of Virology*, vol. 58, No. 2, pp. 583–591, 1986.

Lowe et al., *Proc. Natl. Acad. Sci. (USA)*, vol. 84, pp. 3896–3900, 1987.

Mavromara-Nazos et al., *Journal of Virology*, vol. 60, No. 2, pp. 807–812, 1986.

Meignier et al., *The Journal of Infectious Diseases*, vol. 158, No. 3, pp. 602–614, 1988.

Poffenberger et al., *Journal of Virology*, vol. 53, No. 2, pp. 587–595, 1985.

Silver, et al., *Mol. Cell. Biol.*, vol. 5, No. 3, pp. 518–528, 1985.

HERPES SIMPLEX VIRUS AS A VECTOR

CROSS-REFERENCE TO RELATED APPLICATION

This is a continuation of copending, commonly assigned application Ser. No. 07/455,771 filed Dec. 28, 1989, now abandoned, which is a continuation of application Ser. No. 06/616,930 filed Jun. 4, 1984, now abandoned.

BACKGROUND OF THE INVENTION

1. Field of the Invention

This invention relates to expression vectors and, more particularly, this invention relates to the use of a viral genome as a vector for expression of foreign genes.

2. Brief Description of the Prior Art

Infection of susceptible cells with certain viruses, such as the Herpes Simplex virus (HSV), for example, typically results in shut-off of host protein synthesis. The shut-off occurs in two stages. The initial stage is very likely caused by a structural protein of the virus, and genetic studies indicate that this activity is not essential for virus growth. A second, irreversible inhibition occurs during the viral reproductive cycle as a consequence of expression of viral gene products. Available data based on chemical enucleation with actinomycin D or physical enucleation with the aid of cytocholasin B suggests that the inhibition is at least in part at the translational level.

Although Herpes Simplex virus, type 1 (HSV-1) was previously known to induce some host genes, and particularly foreign genes such as ovalbumin, for example, placed under control of viral regulatory regions and introduced into cells by transfection, their expression is selective and transient. It was previously believed that the inhibitory machinery of wild type virus would not permit sustained expression of a foreign gene introduced into the viral genome.

SUMMARY OF THE INVENTION

According to the present invention, a foreign gene is inserted into a viral genome under the control of promoter-regulatory regions of the genome; the viral genome thus becomes a vector for expression of the foreign gene in infected cells. Such expression is regulated by the promoter-regulatory regions of the genome.

Thus, a viral genome is genetically engineered to render it useful for serial propagation of the gene along with the viral genome and for the sustained expression of foreign genes in a suitable host notwithstanding the shut-off of protein synthesis directed by host chromosomes.

The invention is exemplified by the use of HSV-1 as a vector for the expression of hepatitis B surface antigen (HBsAg). In order to enable and to regulate its expression, the HBsAg gene is placed under the control of HSV gene promoter-regulatory regions. This construct is then inserted into the thymidine kinase (TK) gene of the viral genome. Additionally, a deletion may be made in the TK gene in order to inactivate it. The resulting DNA construct is cotransfected with the intact DNA of a suitable HSV-1 strain, and TK- progeny are selected. Such progeny are found to contain recombinants containing both the deletion and the HBsAg insert. Cultures of such recombinants are found to effectively produce HBsAg over sustained time periods.

According to the invention, a DNA construct, a viral vector containing the DNA construct useful for expression of foreign genes, a method of preparing such a construct and vector, a method of expression using the vector, and specific plasmids and recombinant viruses are provided.

This invention makes possible simultaneous introduction and synchronous expression of foreign genes in large scale cell cultures without prior selection of uniquely transformed genes. It makes possible the expression of genes which normally are poorly expressed, and genes of organisms that are either hazardous or cannot be cultivated in culture.

Other objects and advantages of the invention will be apparent to those skilled in the art from the following detailed description, taken in conjunction with the Figures and the appended claims.

DETAILED DESCRIPTION OF THE INVENTION

General Statement of the Invention

Figure 1:
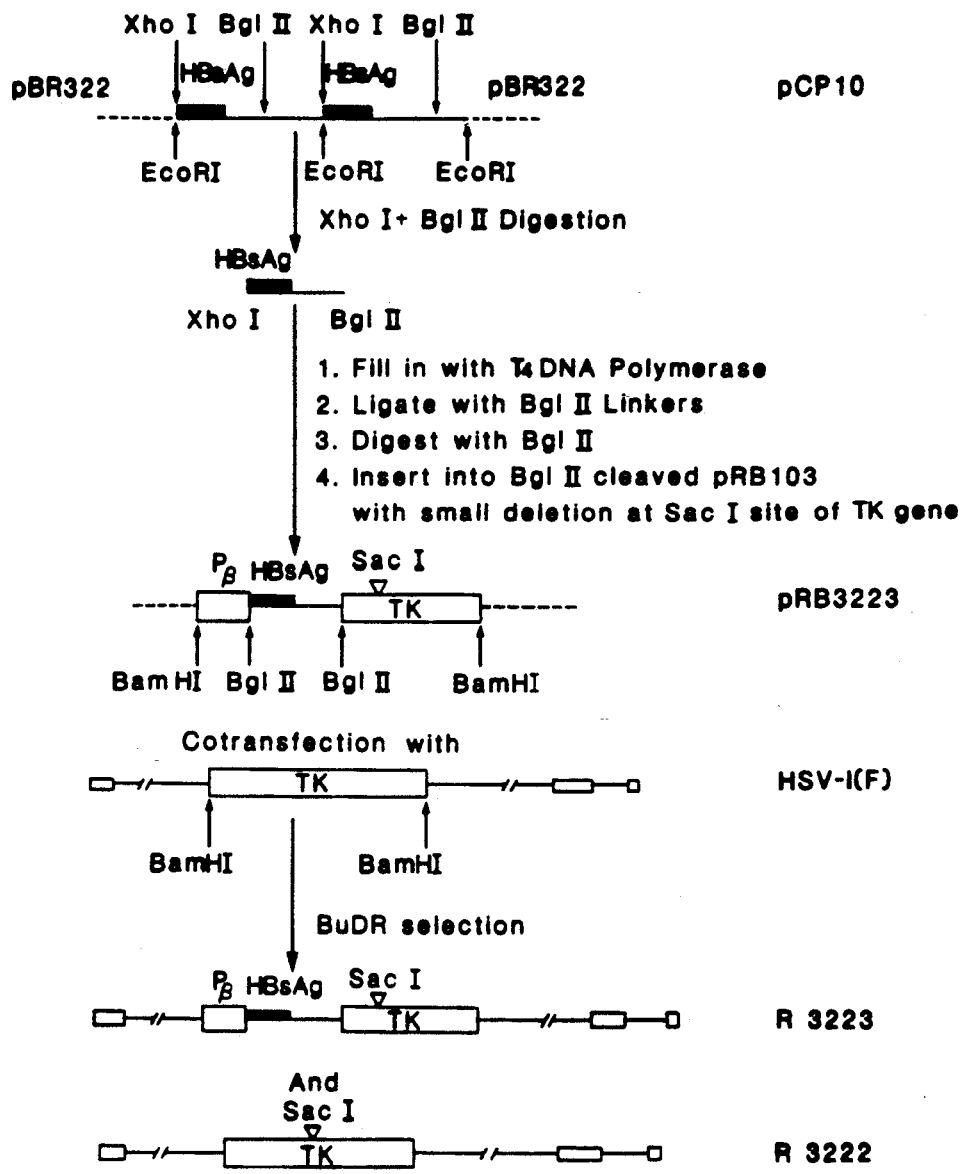
FIG. 1 is a flow sheet schematically illustrating the construction of a recombinant Herpes Simplex virus containing a $\beta$-TK promoter-regulated hepatitis B surface antigen gene.

To convert a Herpes Simplex virus (HSV) to a vector according to the invention, it is sufficient to recombine into its DNA a foreign gene linked to a suitable viral promoter. The foreign gene must have its own transcription termination-poly-adenylation signal, or a new such signal must be provided.

The foreign gene should contain a complete coding sequence. If the foreign gene terminates beyond the transcription termination signal and if downstream from the transcription termination signal there exists another promoter, then the structural sequences of the TK gene of the HSV must be modified so that the TK gene cannot be expressed from that promoter.

In order to recombine the foreign gene into the virus, it is necessary to have homologous flanking sequences through which the gene would recombine at the desired location and a system for selecting the desired recombinant. In this instance the flanking sequences consist of portions of the domain of the viral TK gene and, because selection for an inactive TK gene is being effected, any nucleotide analog (e.g. a drug) that is uniquely or mainly phosphorylated by the TK gene can be used for selection of the recombinant, TK- virus.

In the case of HSV, the TK gene is a highly desirable location for insertion of the foreign gene because it allows selection of recombinants occurring at very low frequencies. Also, the position of the TK gene within the HSV genome can be changed (by known methods) prior to insertion of the foreign gene.

However, it is not necessary that the insertion of the foreign gene be made in the TK gene; insertion may be made at any available non-lethal site and selected by the use of another selectable marker in the HSV genome.

HSV genes form three major groups designated as $\alpha$, $\beta$ and $\gamma$, the expression of which is coordinately regulated and sequentially ordered in a cascade fashion. It is known that for most $\alpha$ and some $\beta$ genes the promoter and regulatory domains are located upstream from the site of initiation of transcription. Specifically, chimeric genes constructed by fusion of promoter-regulatory domains of $\alpha$ gene (e.g., the gene specifying infected cell protein (ICP) Nos. 0, 4, 27 or 22) to the 5' transcribed non-coding and coding sequences of other genes are regulated as $\alpha$ or $\beta$ genes, respectively.

Therefore, according to the invention, a DNA construct is prepared wherein a foreign gene containing its complete structural sequence, flanked on one end with a promoter-regulatory region of a viral gene and on the other with a suitable transcription termination signal, is permanently integrated into a HSV genome.

Such a construct will have the ability to perpetuate the foreign gene in the viral genome, and to express the foreign gene in cells infected with the virus carrying the recombined viral genome.

Exemplary Embodiments of the Invention

Genetic Engineering of HSV-1 Vectors Carrying $\alpha$- and $\beta$-Regulated HBsAg In exemplary embodiments of the invention, the structural sequence and 25 base pairs of the 5' transcribed non-coding region of the gene specifying HBsAg is placed under the control of the $\alpha$ promoter of ICP4 or the $\beta$ promoter of the viral thymidine kinase (TK) genes of an HSV-1 genome by fusion of the 5' transcribed non-coding region and coding region of the HBsAg gene to the respective promoter-regulatory regions of the HSV-1 genes. The chimeric constructs are then inserted into the 5' transcribed non-coding region of the TK gene by homologous recombination through flanking sequences. Cells infected with recombinants carrying the chimeric genes are found to produce and excrete HBsAg into extra-cellular medium for at least 12 hours.

The temporal patterns of expression and the observation that HBsAg linked to the $\alpha$-promoter-regulatory region was regulated as an $\alpha$ gene indicate that HBsAg gene chimeras inserted into the virus are regulated as viral genes.

The nucleotide sequence of the TK gene of HSV-1 has been published. See Wagner et al, *Proc. Natl. Acad. Sci. USA,* vol. 78, pp. 1441-1445 (1981) and McKnight, *Nucleic Acids Res.,* Vol. 8, pp. 5949-5964 (1980). The single Bgl II site within the domain of the TK gene is located within the 5' transcribed but not translated region of the TK gene. Deletion at this site does not affect the promoter function of the region located upstream from that site.

Suitable procedures useful for the insertion of a foreign gene into an HSV-1 genome and the deletion of a portion of the HSV-1 TK gene according to the invention are described by Mocarski et al, *Cell,* Vol. 22, pp. 243-255 (1980); Post et al, *Proc. Natl. Acad. Sci. USA,* Vol. 77, No. 7, pp. 4201-4205 (1980); Post et al, *Cell,* Vol. 24, pp. 555-565 (1981); and Post et al, *Cell,* Vol. 25, pp. 227-232 (1981), as well as in European Patent Publication No. 74,808 (Mar. 23, 1983) and Roizman, et al. U.S. Pat. No. 4,769,331 (Sep. 6, 1988). The disclosures of the foregoing publications are hereby incorporated by reference.

Specifically, both the $\beta$ TK and the $\alpha$ ICP4 regulated HBsAg are inserted into the Bgl II site of the TK gene interrupting the 5' transcribed non-coding region of that gene. The chimeric fragments are then cotransfected with intact HSV DNA, and TK- recombinants carrying the HBsAg gene produced by homologous recombination through flanking sequences are selected by plating on tk- cells in the presence of BuDR, which inactivates the TK+ viral progeny.

Because the DNA fragment carrying the HBsAg gene appears to contain at its terminus 3' to the gene a promoter which substitutes for the TK promoter and maintains the TK+ phenotype, it is necessary to inactivate the TK gene in the chimeric construct by a small deletion at the Sac I site within the coding sequences of that gene.

This procedure allows the construction of HSV containing $\beta$-promoter regulated HBsAg, and is described in more detail below.

Further, to differentiate the expression of $\alpha$-regulated HBsAg from that of $\beta$-recombinant viruses, a construction involving ligation of the promoter-regulatory region of the $\alpha$4 gene of HSV-1 to a DNA fragment containing the HBsAg gene was made. The chimeric gene was cloned into the Bgl II site of the TK gene, and recombined with intact viral DNA by cotransfection to produce a recombinant virus. The details and results are set forth in detail below.

With reference now to FIGS. 1-5, the construction of two recombinant Herpes Simplex viruses containing an inserted coding sequence for hepatitis B surface antigen (HBsAg), and the expression of this protein from the virus, are described in detail.

Construction and Expression of an HSV-1 Recombinant Containing a Chimeric $\beta$-TK Promoter Regulated HBsAg Plasmid pRB 3222 was made from plasmid pRB 103 (deposited on Jun. 4, 1984 as ATCC Accession No. 39718) carrying the Bam HI Q fragment of HSV-1 strain F[HSV-1(F)] (ATCC Accession No. VR733) by Bal 31 exonuclease digestion to remove approximately 200 base pairs at the unique Sac I site in order to inactivate the TK gene. In this construction, the initiation codon for HBsAg is located 25 base pairs downstream from the Xho I site and close to the promoter region of TK gene. Therefore, the $\beta$-regulated gene was about 80 base pairs downstream from the transcription-initiation site derived from the $\beta$ TK gene, whereas the initiation codon for HBsAg in the $\alpha$-regulated gene (below), was about 60 base pairs from the transcription initiation codon derived from the $\alpha$ICP4 gene.

The DNA of plasmid pCP 10 (deposited on Jun. 4, 1984 as ATCC Accession No. 39717) was cleaved with Xho I and Bgl II and the resulting digest was subjected to electrophoresis in 5% polyacrylamide gel. The Xho I-Bgl II fragment (approximately 1.7 kb, which contained the coding sequence for HBsAg) was then purified from the polyacrylamide gel and the termini of DNA fragments were filled with T4 DNA polymerase, ligated to Bgl II linkers, cleaved with Bgl II to produce cohesive ends, and cloned into the Bgl II site of pRB 3222.

The resulting plasmid containing the HBsAg gene in the correct transcriptional orientation relative to the TK promoter-regulatory region (as determined from a Bam HI DNA restriction pattern) is designated herein as pRB 3223 (deposited on Jun. 4, 1984 as ATCC Accession No. 39716).

Recombinant plasmid pRB 3223 was linearized with Pvu II, and 0.1–0.5 μg of the plasmid was then cotransfected with 0.5 μg HSV-1 (F) DNA into rabbit skin cells and plaque purifications of resulting recombinant viruses were carried out as described by Ruyechan et al, J. Virol, Vol. 29, pp. 677–697 (1979). The resulting TK- recombinant viruses were then selected on 143 tk- cell line in the presence of a medium containing mixture 199 lacking thymine but supplemented with 3% calf serum and 40 μg/ml BuDR (bromouracil deoxyriboside).

As predicted, the resulting TK- progeny contained a recombinant which recombined only the deletion in the Sac I site (designated R3222) and another that recombined both the deletion and the HBsAg gene insertion. The latter recombinant is designated R3223 (deposited on Jun. 4, 1984 as ATCC Accession No. VR2086).

Recombinant virus R3223 was differentiated from R3222 by digestion of the recombinant viral DNAs with Eco RI restriction endonuclease. The respective DNA organizations of these viruses were further confirmed by Southern blot analysis.

Table 1, below, and FIG. 2 demonstrate expression and excretion of HBsAg by recombinant virus R3223. Vero cells in 25 cm² flasks were exposed to R3223 (2 pfu/cell) for one hour and then incubated at 37° C. in a medium consisting of maintenance mixture 199 supplemented with 1% calf serum. At the times indicated in Table 1, 5 ml of the maintenance medium in one flask were removed, the cells were washed three times with 5 ml each of phosphate buffered saline (PBS) (0.15 M NaCl, 8.2 mM Na$_2$HPO$_4$, 1.5 mM KH$_2$PO$_4$, and 2.5 mM KCl), harvested in 1 ml of PBS, frozen-thawed three times and centrifuged in an Eppendorf microcentrifuge.

The supernatant fluid containing the cell lysate was then brought to a volume of 5 ml with PBS. Portions containing 200 μl of medium and infected cells were then assayed for the presence of HBsAg with the Abbott Laboratories ELISA diagnostic kit sold under the trademark AUSZYME II, according to the procedure recommended by the manufacturer, as follows.

Extracellular medium and lysates from recombinant and parent virus [HSV-1(F)] infected cells were mixed with beads coated with guinea pig antibody to HBsAg. After incubation, the beads were reacted with peroxidase-conjugated antibody to HBsAg. The presence of HBsAg was measured spectrophotometrically at 492 nm.

As seen in Table 1, as early as four hours post-infection, HBsAg was detected in infected cell lysate but not in the medium. At eight hours postinfection, HBsAg was detected both in lysates of infected cells and in the extracellular medium. At twelve hours postinfection, the bulk of HBsAg was recovered from the extracellular medium. However, the amounts of HBsAg in infected cells were about the same as those detected at earlier times postinfection.

The amounts of HBsAg accumulating in the infected cells reached peak levels approximately 15 fold higher than the background levels obtained with medium and lysates of cells infected with HSV-1(F) at or before 8 hr postinfection and did not significantly increase thereafter. The amounts of HBsAg detected in the extracellular medium increased with time indicating that HBsAg was excreted and accumulated outside the infected cell. The patterns of accumulation of α- and β- regulated HBsAg were similar and in accord with the observation that the kinetics of accumulation of α- and β-regulated TK genes expressed by viruses carrying these genes were also similar.

HBsAg was not detected in wild type [HSV-1(F)] virus infected cells or extracellular medium. The observation that HBsAg is excreted was also shown in cells infected with vaccinia virus carrying the HBsAg gene.

TABLE 1

Expression of α- and β-regulated HBsAg in Cells Infected with Recombinant and Parent Viruses

| Hrs post Infect. | HSV-1(F) | | R3223 | | R3225 | |
|---|---|---|---|---|---|---|
| | Medium | Cell lysate | Medium | Cell lysate | Medium | Cell lysate |
| 4 | 0.08* | 0.07 | 0.42 | 0.57 | 0.58 | 0.56 |
| 8 | 0.08 | 0.07 | 3.69 | 0.95 | 3.31 | 1.06 |
| 12 | 0.09 | 0.07 | 6.33 | 1.26 | 5.06 | 1.20 |

*Optical density units.

Figure 2:
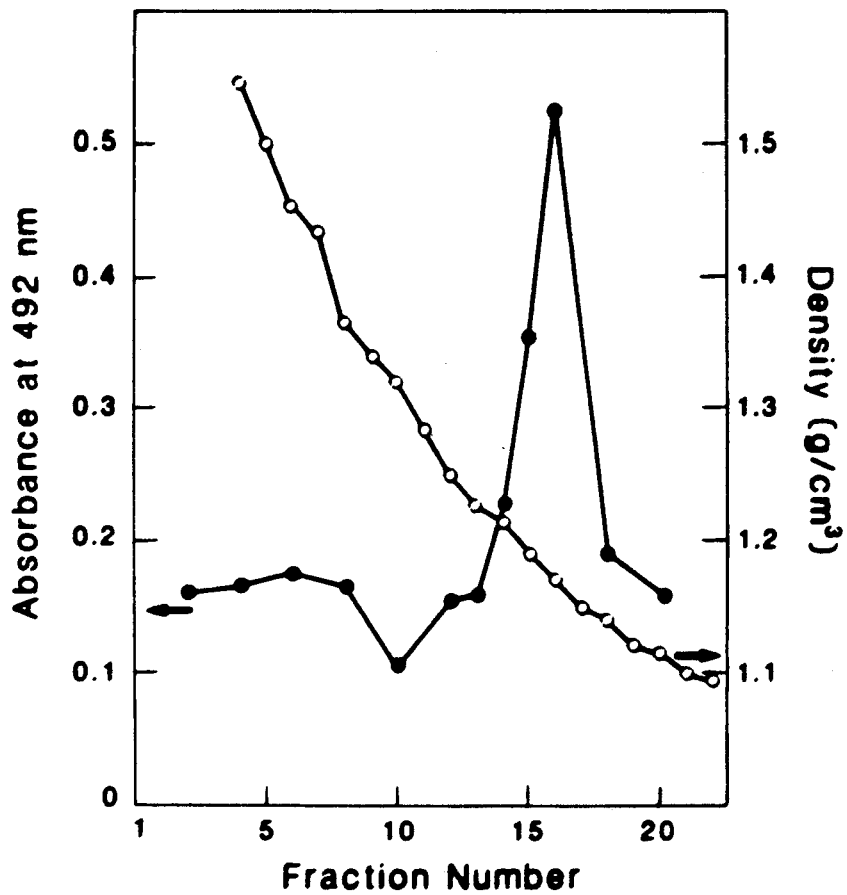
FIG. 2 is a graphical representation demonstrating the buoyant density in cesium chloride gradient of purified expressed HBsAg in cells infected with the virus of FIG. 1.

FIG. 2 graphically represents the results of a study carried out to characterize excreted HBsAg obtained as described above. Vero cells were infected with R3223 at 2 pfu/cell. At 12 hours postinfection, 9 ml of maintenance medium was harvested and centrifuged at 36,000 rpm for 20 hours at 4° C. as Beckman SW41 rotor. The resulting pellet was suspended in 0.5 ml of the same medium and then 200 μl were layered on top of a 1.1–1.5 g/ml isopycnic CsCl density gradient and centrifuged at 36,000 rpm for 36 hours at 25° C. in a Beckman SW41 rotor. Fractions (0.5 ml) were collected from the bottom of the centrifuge tube and diluted with 1:10 with PBS. The fractions were assayed for the presence of HBsAg as detailed above with reference to Table 1.

Figure 3:
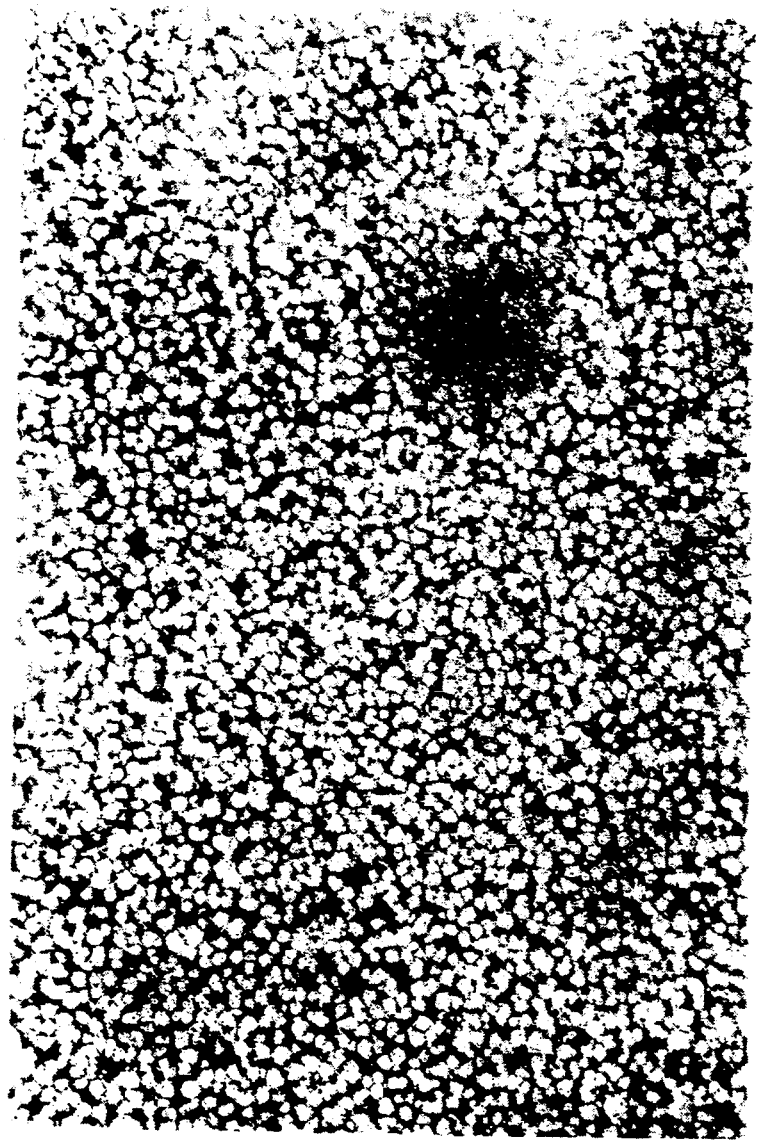
FIG. 3 is an electron micrograph of purified expressed HBsAg obtained from cells infected with the virus of FIG. 1.

As seen in FIG. 2, the HBsAg banded at a density of 1.17 g/ml. It is known that in serum, HBsAg forms spherical particles with diameters between 18 and 25 nm (Dane et al, Lancet, Vol. 1, p. 695, 1970). As seen in FIG. 3, particles similar in dimension (i.e. 18–25 nm) to Dane particles were detected by electron microscope examination of the peak fraction (which was negatively stained with 2% phosphotungstic acid), thus confirming the character of the excreted HBsAg.

The foregoing description details the preparation of a recombinant HSV-1 viral plasmid carrying the coding sequence for HBsAg, and the effective use of the plasmid as a vector for expressing that protein. In the construction of FIGS. 1–3, the HBsAg fragment was placed under the control of a β promoter region of the virus.

Construction and Expression of an HSV-1 Recombinant Containing an αICP4-HBsAg Gene The following describes the construction of a recombinant HSV-1 plasmid and a recombinant virus carrying the HBsAg coding sequence and gene, respectively, under the control of an α promoter.

Figure 4:
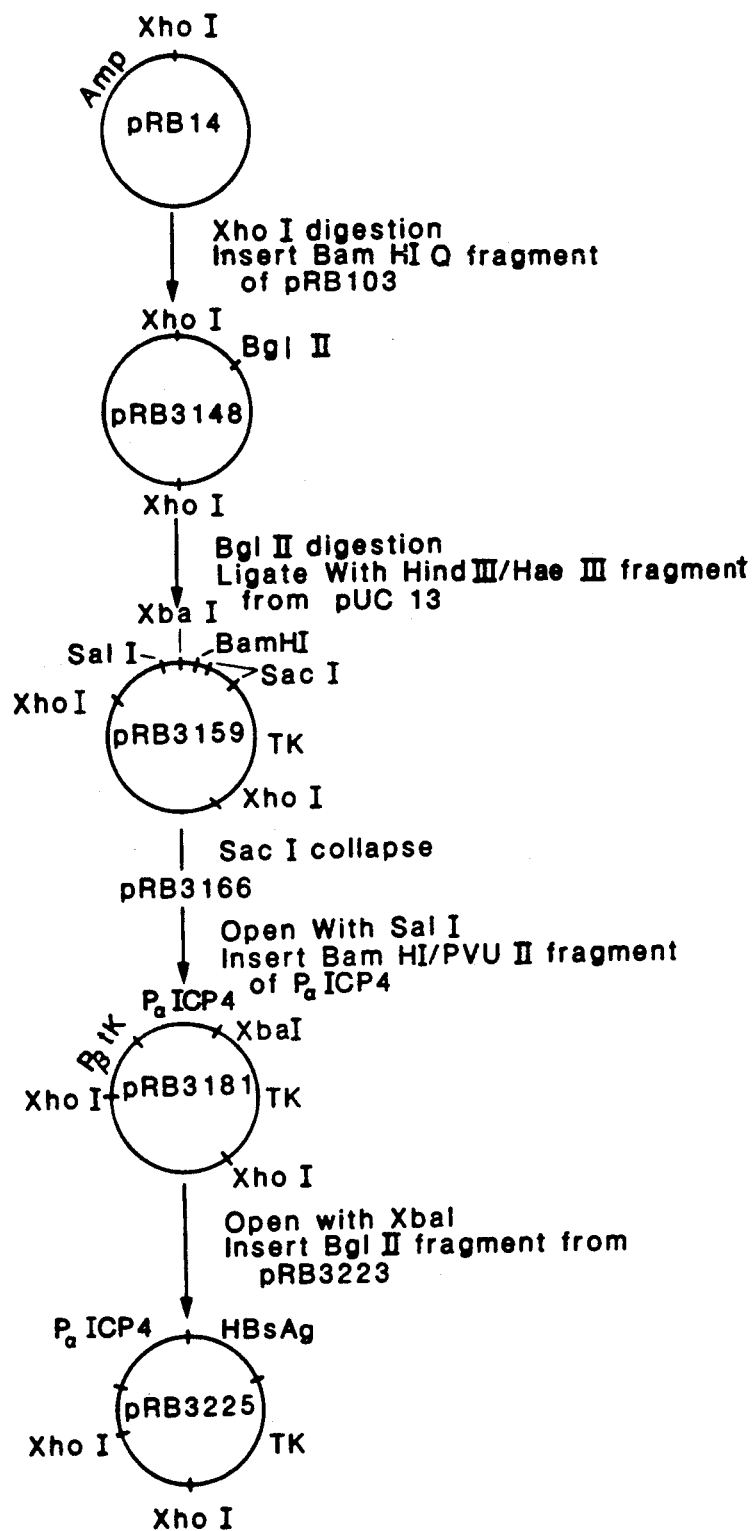
FIG. 4 is a flow sheet schematically illustrating the construction of a recombinant plasmid containing chimeric $\alpha$ICP4-HBsAg gene; and, FIG. 5 is a flow sheet depicting cotransfection of the plasmid of FIG. 4 with intact viral DNA and selection of a recombinant Herpes Simplex virus containing $\alpha$ICP4-HBsAg gene.

FIG. 4 demonstrates the construction of a recombinant Herpes Simplex virus containing chimeric αICP4-HbsAg gene. The construction involved ligation of the promoter-regulatory region of the α4 gene of HSV-1 to the DNA fragment containing the HBsAg gene described above. Specifically, the Bam HI Q fragment containing the HSV-1 (F) TK gene from pRB 103 was inserted into the Xho I site of plasmid pRB 14, which was constructed from pBR 322 (ATCC Accession No. 31344) by replacement of the Eco RI-Pvu II fragment with Xho I linker obtained from New England Biolabs, Cambridge, Mass. USA.

The resulting recombined plasmid is designated herein as pRB 3148. Plasmid pRB 3159 was then constructed by cloning the Hind III-Hae III fragment (containing the polylinker) from pUC 13 into the unique Bgl II site of the HSV-1 (F) Bam HI Q such that the Bam HI site was closest to the structural sequence of the TK gene, whereas the Sal I site was closest to the transcription initiation site of that gene. Plasmid pUC 13 was selected as a suitable source for the fragment containing the polylinker, but suitable polylinkers are commercially available.

Plasmid pRB 3166 was constructed from pRB 3159 by digesting with Sac I and religating to delete the Sac I fragment containing the Bgl II-Sac I fragment of Bam HI Q.

In the last step, two fragments were cloned into pRB 3166 to yield plasmid pRB 3225. First, the Bam HI-Pvu II fragment from pRB 403 (deposited on Jun. 4, 1984 as ATCC Accession No. 39719) containing the promoter-regulatory domain of the αICP4 gene was cloned into the Sal I site of the polylinker sequence such that the transcription initiation site of αICP4 in the Bam HI-Pvu II fragment was close to the Xba I site. Lastly, the Bgl II fragment containing the HBsAg gene from pRB 3223 was cloned into the Xba I site such that the αICP4 promoter and the structural sequences of the HBsAg gene were in the same transcriptional orientation as determined from Eco RI DNA restriction endonuclease patterns. Thus, by the foregoing procedure, chimeric gene P$\alpha_4$-HBsAg was cloned into the Bgl II site of the TK gene.

Figure 5:
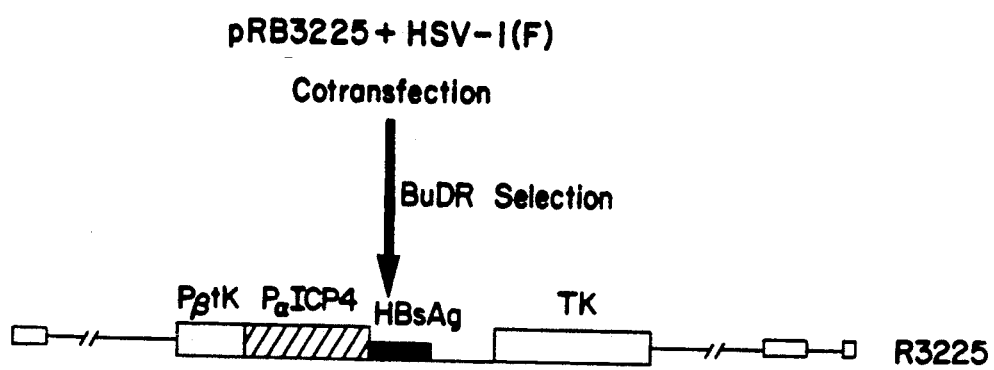

The resulting recombinant plasmid pRB 3225 (ATCC Accession No. 39715) was cotransfected with intact HSV-1 (F) DNA in 143 tk- cells as described above with reference to FIG. 1, and the resulting recombinant virus R3225 (deposited on Jun. 4, 1984 ATCC Accession No. VR2087) containing a P$\alpha$ 4-HBsAg fragment in the TK gene was selected from the TK- progeny in 143 tk- cells and checked for HBsAg expression as set forth below. The transfection and selection step is depicted schematically in FIG. 5.

To differentiate the expression of α-regulated HBsAg (R3225) from that of β-regulated HBsAg (R3223) recombinant viruses, the observation that α genes are transcribed in the absence of de-novo protein synthesis postinfection, whereas α genes require the presence of functional α genes for their expression, was utilized according to the following procedure.

Replicate Hep-2 cell cultures in 25 cm$^2$ flasks were preincubated for 1 hr. in maintenance medium containing 50 µg/ml of cycloheximide (+cyclo), and then infected at 20/pfu per cell with wild type [HSV-1(F)], R3222, R3223 or R3225 viruses, respectively. Five hours postinfection, the medium containing cycloheximide was removed and the cells were extensively washed and then incubated in medium containing antinomycin D (10 µg/ml). The cells and medium were harvested after 90 minutes of additional incubation. Medium and cell lysate were assayed for HBsAg by the AUSZYME II diagnostic kit (Abbott Laboratories).

The control experiments (-cyclo) followed same washing procedure except that no drugs were added. Results are given in Table 2, below.

TABLE 2

| Regulation of HBsAg Expressed by Recombinant Viruses | | | | | |
|---|---|---|---|---|---|
| Conditions of infection | Materials tested | HSV-1 (F) | R3222 | R3223 | R3225 |
| −Cycloheximide | medium | <0.06* | <0.06 | 5.22 | 2.34 |
| −Cycloheximide | cell lysate | <0.06 | <0.06 | 3.09 | 1.04 |
| +Cycloheximide | medium | <0.06 | <0.06 | <0.06 | 0.77 |
| +Cycloheximide | cell lysate | <0.06 | <0.06 | <0.06 | 0.80 |

*Optical density units.

As shown above in Table 2, HBsAg was made by cells infected with R3225 but not with R3223 after removal of inhibitory concentrations of cycloheximide present in the medium during infection and for five hours postinfection.

A characteristic of HSV-1 α genes is that they are the only viral genes transcribed in cells exposed during and after infection to inhibitors of protein synthesis. As shown in Table 2, above, only the HBsAg gene contained in R3225 was expressed in cells infected and maintained in the presence of cycloheximide and then released from the inhibitory effects of cycloheximide in the presence of actionomycin D to preclude the transcription of β genes dependent on the synthesis of the αICP4 gene product.

Discussion of Results

The foregoing demonstrates that the HSC genome can act as an expression vector for foreign genes and, in particular, for HBsAg.

Although HSV shuts off host macromolecular metabolism and especially host protein synthesis, it does not adversely affect the expression of foreign genes (as exemplified by HBsAg) inserted into the viral genome and regulated by HSV promoter-regulatory regions. The antigenicity of the gene product, its buoyant density in CsCl density gradients and the characteristic 18-25 nm particle size present in the banded preparations demonstrate that the product of the HBsAg gene carried by HSV is an authentic product of that gene. The observation that HBsAg is excreted from the infected cell suggests that the antigen is processed properly for exportation from cells.

The results presented herein indicate that both the αICP4 and the βTK linked HBsAg genes expressed the antigen for at least 12 hours. The patterns of synthesis of the HBsAg and the observation that αICP4 linked was regulated as an α gene indicate that the chimeric HBsAg genes in the HSV-1 vector were regulated as viral genes. The production of HBsAg can be especially heightened by insertion of the gene under an α promoter-regulatory region into the genome of ts mutants in the ICP4 gene inasmuch as such mutants have been shown to express αgenes continuously in cells infected and maintained at the non-permissive temperature.

Use of the HSV genome as a vector for foreign genes is particularly useful for the biosynthesis in human cells and characterization of products of (a) genes of viruses whose growth is restricted in cell culture (e.g., hepatitis B virus), (b) genes of infectious agents that are particularly hazardous for humans, and (c) cellular genes expressed at very low levels, or not at all, in cultured cells. HSV-1 expression vectors would also be useful for analyses of gene regulation, especially at the translational level.

A particular advantage of HSV-vectors relates to the fact that these viruses have a very wide host range; infection of many different types of cells in a uniform manner is made possible. Therefore, foreign genes inserted into an HSV-1 vector can be readily propagated serially in culture and will be packaged as part of the viral genome in virus particles. The vector can then be used to infect synchronously large scale cell cultures to obtain sustained expression of the foreign gene in all of the infected cells. This method has considerable advantage over other methods which rely upon transfection of cells with DNA and selection of a small minority of cells which express the foreign gene. This procedure is applicable for human diploid cell strains authorized for human vaccine production (e.g. MRC-5 or W138) which do not lend themselves to transformation by DNA fragments for expression of foreign genes.

In the exemplary illustration given herein, the HBsAg was inserted into wild type genomes modified at the site of insertion of the HBsAg gene. Although as much as 7 Kbp of DNA has been inserted previously (Knipe et al, *Proc. Natl. Acad. Sci.*, Vol. 75, pp. 3896–3900, 1978), the capacity of wild type HSV DNA to carry additional gene products might be limited.

The construction of mutant HSV-1(F)I358 from which approximately 14 Kbp of DNA contained within the internal reiterated sequences had been replaced with a 2 Kbp insert has previously been reported (Poffenberger et al, *Proc. Natl. Acad. Sci.*, Vol. 80, pp. 2690–2694, 1983). By replacing the insert and expanding the genome to its known maximum capacity, the I358 mutant could carry as much as 23 Kbp of foreign DNA. HSV-1(F)I358 has the capacity therefore to serve as a vector of several genes specifying antigens from a variety of human infectious agents for immunoprophylaxis.

The DNA of Herpes Simplex virus, type 2, (HSV-2) is essentially identical in structure to that of HSV-1, and differs only in nucleotide matching of base pairs. Therefore, DNA constructs identical to those illustrated herein using the HSV-1 genome are feasible according to the present invention.

Herpes Simplex virus 1 is readily available to the public. It is, for example, on deposit with the American Type Culture Collection, 12301 Parklawn Drive, Rockville, Md. 20852, USA, under ATCC Accession Number VR733. Likewise, plasmid pBR322 is readily available to the public; it too is on deposit at the ATCC, under ATCC Accession Number 31344. The ATCC has been requested to maintain these cultures, inter alia, in accordance with the requirements of the Implementing Regulations to the European Patent Convention, as well as the remaining cultures identified herein by ATCC Accession Numbers, which have been deposited.

The remaining materials identified herein are publicly available. For example, the restriction enzymes, T4 DNA ligase, polynucleotide kinase, T4 DNA polymerase, exonuclease Bal 31, and restriction enzyme linkers were purchased from New England Biolabs, Cambridge, Mass. USA and used as directed by the manufacturer. DNA probes for screening *E. coli* colonies for desired recombinant plasmids were labeled by nick translation with [$\gamma$-$P^{32}$]-ATP obtained from New England Nuclear, Cambridge, Mass. USA.

The F strain of HSV-1[HSV-1(F)] and all recombinants derived herein were grown and titered on Vero or HEp-2 cell lines obtained from American Type Culture Collection. The rabbit skin cells used for transfection with viral DNA, as well as the human tk-cell line used for selection of TK- recombinants, are publicly available.

The foregoing detailed description is given for clearness of understanding only, and no unnecessary limitations should be inferred therefrom, as modifications within the scope of the invention will be obvious to those skilled in the art.

I claim:

1. A recombinant viral genome of a *Herpes simplex* virus (HSV) containing an expressable non-HSV nucleotide sequence encoding a desired protein permanently integrated at a non-lethal site of said genome.

2. The recombinant viral genome of claim 1 wherein said *Herpes simplex* virus is HSV-1.

3. The recombinant viral genome of claim 1 wherein said non-lethal site and said sequence are selected by the use of a selectable marker in said genome.

4. The recombinant viral genome of claim 2 wherein said marker is the thymidine kinase (TK) gene of said genome.

5. The recombinant viral genome of claim 3 wherein said sequence is flanked at its respective ends with a suitable transcription termination signal and a promoter-regulatory region comprising an HSV alpha gene promoter.

6. The recombinant viral genome of claim 5 wherein said promoter-regulatory region comprises an alpha gene promoter of an infected cell protein gene.

7. The recombinant viral genome of claim 6 wherein said promoter-regulatory region comprises an alpha gene promoter of an infected cell protein number 4 gene.

8. The recombinant viral genome of claim 3 wherein said sequence is flanked at its respective ends with a suitable transcription termination signal and a promoter-regulatory region comprising an HSV beta gene promoter.

9. The recombinant viral genome of claim 8 wherein said beta gene promoter is a promoter of the thymidine kinase gene of said genome.

10. The recombinant viral genome of claim 1 wherein said sequence comprises a structural coding sequence of hepatitis B surface antigen (HBsAg).

11. The recombinant viral genome of claim 1 wherein said *Herpes simplex* virus is HSV-2.

12. A plasmid vector containing an expressable non-HSV nucleotide sequence encoding a desired protein permanently integrated at a non-lethal site of a viral genome of a *Herpes simplex* virus (HSV).

13. The plasmid vector of claim 12 comprising plasmid pRB 3223 (ATCC Accession No. 39716).

14. The plasmid vector of claim 12 comprising plasmid pRB 3225 (ATCC Accession No. 39715).

15. The plasmid vector of claim 12 wherein said *Herpes simplex* virus is HSV-1.

16. The plasmid vector of claim 12 wherein said non-lethal site and said sequence are selected by the use of a selectable marker in said genome.

17. The plasmid vector of claim 16 wherein said marker is the thymidine kinase (TK) gene of said genome.

18. The plasmid vector of claim 16 wherein said sequence is flanked at its respective ends with a suitable transcription termination signal and a promoter-regulatory region comprising an HSV alpha gene promoter.

19. The plasmid vector of claim 18 wherein said promoter-regulatory region comprises an alpha gene promoter of an infected cell protein.

20. The plasmid vector of claim 19 wherein said promoter-regulatory region comprises an alpha gene promoter of an infected cell protein number 4 gene.

21. The plasmid vector of claim 16 wherein said sequence is flanked at its respective ends with a suitable transcription termination signal and a promoter-regulatory region comprising an HSV beta gene promoter.

22. The plasmid vector of claim 21 wherein said beta gene promoter is a promoter of the thymidine kinase gene of said genome.

23. The plasmid vector of claim 12 wherein said sequence comprises a structural coding sequence for hepatitis B surface antigen (HBsAg).

24. The plasmid vector of claim 12 wherein said *Herpes simplex* virus is HSV-2.

25. A recombinant virus comprising a product of cotransfection of the plasmid vector of claim 12 with intact *Herpes simplex* virus DNA in a suitable host and screening of resulting progeny for progeny containing said sequence.

26. The recombinant virus of claim 25 comprising recombinant virus R3223 (ATCC Accession No. VR2086).

27. The recombinant virus of claim 25 comprising recombinant virus R3225 (ATCC Accession No. VR2087).

28. The recombinant virus of claim 25 wherein said non-lethal site and said sequence are selected by the use of a selectable marker in said genome, and said progeny are screened by selection for the presence or absence of said marker.

29. A method of obtaining a desired protein, comprising the steps of:
   (a) preparing a plasmid vector according to claim 12 wherein said expressible non-HSV nucleotide sequence codes for the expression of said protein;
   (b) cotransfecting said plasmid vector with intact *Herpes simplex* virus DNA to produce viral progeny;
   (c) screening and isolating progeny containing said sequence to obtain a recombinant virus; and,
   (d) infecting a suitable host with said recombinant virus and culturing said infected cells whereby said protein is produced.

30. The method of claim 29 including the further steps of harvesting and purifying said protein.

31. The method of claim 29 wherein said Herpes Simplex virus of said vector is HSV-1.

32. The method of claim 29 wherein said non-lethal site and said sequence are selected by the use of a selectable marker in said genome, and said screening step (c) is carried out by selecting for the presence or absence of said marker.

33. The method of claim 32 wherein said marker is the thymidine kinase (TK) gene of said genome.

34. The method of claim 32 wherein said sequence is flanked at its respective ends with a suitable transcription termination signal and a promoter-regulatory region comprising an HSV alpha gene promoter.

35. The method of claim 34 wherein said promoter-regulatory region comprises an alpha gene promoter of an infected cell protein gene.

36. The method of claim 35 wherein said promoter-regulatory region comprises an alpha gene promoter of an infected cell protein number 4 gene.

37. The method of claim 32 wherein said sequence is flanked at its respective ends with a suitable transcription termination signal and a promoter-regulatory region comprising an HSV beta gene promoter.

38. The method of claim 37 wherein said beta gene promoter is a promoter of the thymidine kinase gene of said genome.

39. The method of claim 29 wherein said sequence comprises a structural coding sequence for hepatitis B surface antigen (HBsAg).

40. The method of claim 29 wherein said Herpes Simplex virus of said vector is HSV-2.

41. A method of preparing a recombinant viral genome of a Herpes Simplex virus (HSV), said method comprising the steps of:
   (a) isolating a viral genome of said Herpes Simplex virus; and,
   (b) permanently integrating into said genome at a non-lethal site thereof an expressable non-HSV nucleotide sequence encoding a desired protein.

42. The method of claim 41 wherein said Herpes Simplex virus is HSV-1.

43. The method of claim 41 wherein said non-lethal site and said sequence are selected by the use of a selectable marker in said genome.

44. The method of claim 43 wherein said marker is the thymidine kinase (TK) gene of said genome.

45. The method of claim 43 wherein said sequence is flanked at its respective ends with a suitable transcription termination signal and a promoter-regulatory region comprising an HSV alpha gene promoter.

46. The method of claim 45 wherein said promoter-regulatory region comprises an alpha gene promoter of an infected cell protein.

47. The method of claim 46 wherein said promoter-regulatory region comprises an alpha promoter of an infected cell protein number 4 gene.

48. The method of claim 41 wherein said sequence is flanked at its respective ends with a suitable transcription termination signal and a promoter-regulatory region comprising an HSV beta gene promoter.

49. The method of claim 48 wherein said beta gene promoter is a promoter of the thymidine kinase gene of said genome.

50. The method of claim 41 wherein said sequence comprises a structural coding sequence for hepatitis B surface antigen (HBsAg).

51. The method of claim 41 wherein said Herpes Simplex virus is HSV-2.

52. A method of obtaining a recombinant virus, comprising the steps of :
   (a) cotransfecting the plasmid vector of claim 12 with intact Herpes Simplex virus DNA in a suitable host; and,
   (b) screening the resulting progeny for a recombinant virus containing said expressible non-HSV nucleotide sequence.

53. The method of claim 52 wherein said Herpes Simplex virus is HSV-1.

54. The method of claim 52 wherein said non-lethal site and said sequence are selected by the use of a selectable marker in said genome, and said screening step (b) is carried out by selecting for the presence or absence of said marker.

55. The method of claim 54 wheren said marker is the thymidine kinase (TK) gene of said genome.

56. The method of claim 54 wherein said sequence is flanked at its respective ends with a suitable transcription termination signal and a promoter-regulatory region comprising an HSV alpha gene promoter.

57. The method of claim 56 wherein said promoter-regulatory region comprises an alpha gene promoter of an infected cell protein.

58. The method of claim 57 wherein said promoter-regulatory region comprises an alpha gene promoter of an infected cell protein number 4 gene.

59. The method of claim 54 wherein said sequence is flanked at its respective ends with a suitable transcription termination signal and a promoter-regulatory region comprising an HSV beta gene promoter.

60. The method of claim 59 wherein said beta gene promoter is a promoter of the thymidine kinase gene of said genome.

61. The method of claim 52 wherein said sequence comprises a structural coding sequence for hepatitis B surface antigen (HBsAg).

62. The method of claim 52 wherein said Herpes Simplex virus of said vector is HSV-2.

* * * * *

UNITED STATES PATENT AND TRADEMARK OFFICE
CERTIFICATE OF CORRECTION

PATENT NO.    : 5,288,641
DATED         : February 22, 1994
INVENTOR(S)   : Bernard Roizman It is certified that error appears in the above-identified patent and that said Letters Patent is hereby corrected as shown below:

Col. 4, line 13, "tk -" should read - - TK- - -.

Col. 4, line 27, "$\beta$-recombinant" should read - - $\beta$-regulated HBsAg recombinant - -.

Col. 6, line 66, "$\alpha$ICP4-HbsAg" should read - - $\alpha$ICP4-HBsAg - -.

Col. 8, line 33, "HSC" should read - - HSV - -.

Col. 10, line 13, "expressable" should read - - expressible - -.

Col. 10, line 21, "claim 2" should read - - claim 3 - -.

Col. 10, line 49, "expressable" should read - - expressible - -.

Col. 12, line 19, "expressable" should read - - expressible - -.

Signed and Sealed this

Twelfth Day of July, 1994

Attest:

BRUCE LEHMAN

*Attesting Officer*   *Commissioner of Patents and Trademarks*